United States Patent
Erlebach

(10) Patent No.: US 10,597,208 B2
(45) Date of Patent: Mar. 24, 2020

(54) BIODEGRADABLE PERSONAL CARE SYSTEMS

(71) Applicant: On The Go Products Co., Caldwell, ID (US)

(72) Inventor: Luke Erlebach, Caldwell, ID (US)

(73) Assignee: On The Go Products Co., Caldwell, ID (US)

(*) Notice: Subject to any disclaimer, the term of this patent is extended or adjusted under 35 U.S.C. 154(b) by 0 days.

(21) Appl. No.: 15/884,798

(22) Filed: Jan. 31, 2018

(65) Prior Publication Data
US 2018/0215518 A1 Aug. 2, 2018

Related U.S. Application Data

(60) Provisional application No. 62/452,777, filed on Jan. 31, 2017.

(51) Int. Cl.
*B65D 65/46* (2006.01)
*B65D 77/04* (2006.01)
(Continued)

(52) U.S. Cl.
CPC ........... *B65D 65/466* (2013.01); *A45D 40/00* (2013.01); *A47K 10/18* (2013.01); *A61F 15/001* (2013.01);
(Continued)

(58) Field of Classification Search
CPC .............. B65D 65/466; B65D 83/0805; B65D 2209/00; Y02W 90/11–14; A61F 15/001;
(Continued)

(56) References Cited

U.S. PATENT DOCUMENTS 4,286,639 A * 9/1981 Murphy ............... A61F 15/001
150/131
4,917,238 A * 4/1990 Schumacher .......... A47L 13/51
206/223
(Continued)

FOREIGN PATENT DOCUMENTS

EP 0710606 A1 5/1996
JP 2003175942 A 6/2003

OTHER PUBLICATIONS

Levy, Sandra, "Innovative wipes packaging: coming to a store near you: groundbreaking solutions are worth writing home about"; Nonwovens Industry; (Apr. 2010); 5 pages; vol. 41, Issue 4; [Retrieved online Oct. 14, 2016; Retrieved from <URL: http://dialog.proques.com/professional/docview/1065411700/1572A2DE619355F213F/14?accountid=157282>].
(Continued)

*Primary Examiner* — Chun Hoi Cheung
*Assistant Examiner* — Brijesh V. Patel
(74) *Attorney, Agent, or Firm* — Thorpe North & Western, LLP

(57) ABSTRACT

A biodegradable personal care system which has a biodegradable housing, a biodegradable airtight container positioned in the biodegradable housing, and biodegradable moist wipes positioned inside the biodegradable airtight container. The biodegradable airtight container can be resealable. The biodegradable personal care system can further include a biodegradable dry wipe positioned in a dry wipe container in the biodegradable housing.

13 Claims, 3 Drawing Sheets

(51) Int. Cl.
*A61M 35/00* (2006.01)
*A61F 15/00* (2006.01)
*A47K 10/18* (2006.01)
*A45D 40/00* (2006.01)
*A61F 9/04* (2006.01)

(52) U.S. Cl.
CPC ........... *A61M 35/003* (2013.01); *B65D 77/04* (2013.01); *A45D 2200/051* (2013.01); *A61F 9/04* (2013.01); *A61M 2209/06* (2013.01); *Y02W 90/13* (2015.05)

(58) Field of Classification Search
CPC ...... A61F 15/003; A61F 13/84; A61F 13/551; A61F 13/5519; A61F 13/55175
USPC ......... 206/581, 494, 38, 440, 223, 233, 438, 206/812, 823, 363, 37; 383/1, 11, 106, 383/113; 604/385.06, 385.02, 292
See application file for complete search history.

(56) References Cited

U.S. PATENT DOCUMENTS

| | | | | |
|---|---|---|---|---|
| 5,217,164 A * | 6/1993 | Sullivan | ................ | B65D 3/262 206/385 |
| 5,242,057 A * | 9/1993 | Cook | ................ | A47K 10/421 206/233 |
| 5,261,531 A * | 11/1993 | Nieves | ................ | A61F 13/5519 206/205 |
| 5,286,538 A | 2/1994 | Pearlstein et al. | | |
| 5,512,333 A | 4/1996 | Suskind | | |
| 5,531,325 A * | 7/1996 | Deflander | ................ | A47K 10/20 206/494 |
| 5,556,026 A | 9/1996 | Blankitny | | |
| 5,569,230 A * | 10/1996 | Fisher | ................ | A61F 13/47218 206/438 |
| 5,579,916 A * | 12/1996 | Manko | ................ | A45C 11/008 132/312 |
| 5,629,081 A | 5/1997 | Richards et al. | | |
| 5,884,771 A * | 3/1999 | McCormick | ........... | B65D 85/00 206/38 |
| 6,004,059 A * | 12/1999 | Zaccaria | ............ | A46B 11/0003 401/268 |
| 6,601,737 B1 * | 8/2003 | Sandler | ................ | A45D 34/06 206/229 |
| 6,960,374 B1 * | 11/2005 | Terada | ................ | B32B 9/00 428/35.7 |
| 7,104,977 B2 * | 9/2006 | Price | ................ | A41B 9/00 206/581 |
| 7,144,391 B1 * | 12/2006 | Kreutz | ................ | A61F 13/2051 604/385.17 |
| 7,179,245 B2 | 2/2007 | Giori | | |
| 7,699,166 B2 * | 4/2010 | Gauger | ................ | B65D 75/20 206/229 |
| 8,071,524 B2 | 12/2011 | Horton | | |
| 8,607,972 B2 * | 12/2013 | Maclean | ................ | A61F 17/00 206/223 |
| 8,636,143 B1 * | 1/2014 | Hebert | ................ | A45C 3/06 206/223 |
| 9,151,005 B1 | 10/2015 | Hao | | |
| 2003/0217946 A1 * | 11/2003 | Hsu | ................ | B65D 83/0805 206/494 |
| 2005/0120915 A1 * | 6/2005 | Bowden | ................ | B65D 65/466 106/162.5 |
| 2005/0228355 A1 * | 10/2005 | Briggs | ................ | A61F 15/001 604/385.06 |
| 2006/0151351 A1 * | 7/2006 | Hughes | ................ | B65D 75/5805 206/494 |
| 2007/0055213 A1 * | 3/2007 | Erekson | ............ | A61F 13/15252 604/385.13 |
| 2007/0272588 A1 * | 11/2007 | Longacre | ................ | B65D 27/28 206/581 |
| 2010/0000897 A1 * | 1/2010 | Bumpass | ................ | A61F 13/26 206/440 |
| 2013/0053293 A1 * | 2/2013 | Dituro | ................ | B65D 65/466 510/277 |
| 2013/0243912 A1 * | 9/2013 | Jensen | ................ | B65D 77/20 426/124 |
| 2014/0056543 A1 * | 2/2014 | Lay | ................ | B65D 65/466 383/1 |
| 2015/0251816 A1 * | 9/2015 | Elkins | ................ | B65F 1/002 383/64 |
| 2015/0344208 A1 * | 12/2015 | Maloux | ................ | B65D 77/0486 426/112 |
| 2016/0052692 A1 * | 2/2016 | Branham | ................ | B65D 27/00 220/592.01 |
| 2017/0081096 A1 * | 3/2017 | Rossomando | ........ | B65D 65/466 |

OTHER PUBLICATIONS

Stall Mates; "Individually Wrapped Travel Wipes, 30 pack"; Stall Mates Flushable Wipes; (2016); 6 pages; Retrieved online Oct. 14, 2016; Retrieved from <URL: https://thrivemarket.com/stallmates-individually-wrapped-travel-wipes?&ccode_force=1?&ccode=0SHIP8161 >].

* cited by examiner

BIODEGRADABLE PERSONAL CARE SYSTEMS

CROSS-REFERENCE TO RELATED APPLICATIONS

This application claims the benefit of U.S. Provisional Patent Application Ser. No. 62/452,777 filed on Jan. 31, 2017, which is herein incorporated by reference in its entirety.

BACKGROUND

People often spend a significant amount of time traveling; whether it is local, regional, national, or international, many people are always traveling. As people continue to spend more time away from their homes, convenient access to personal care and hygiene items become more important, and this need, along with airline policies, has resulted in a market of miniature (3.4 oz or smaller), travel-sized products.

BRIEF DESCRIPTION OF THE DRAWINGS

For a fuller understanding of the nature and advantage of the present invention, reference is being made to the following detailed description of preferred embodiments and in connection with the accompanying drawings, in which.

DETAILED DESCRIPTION

Figure 1:
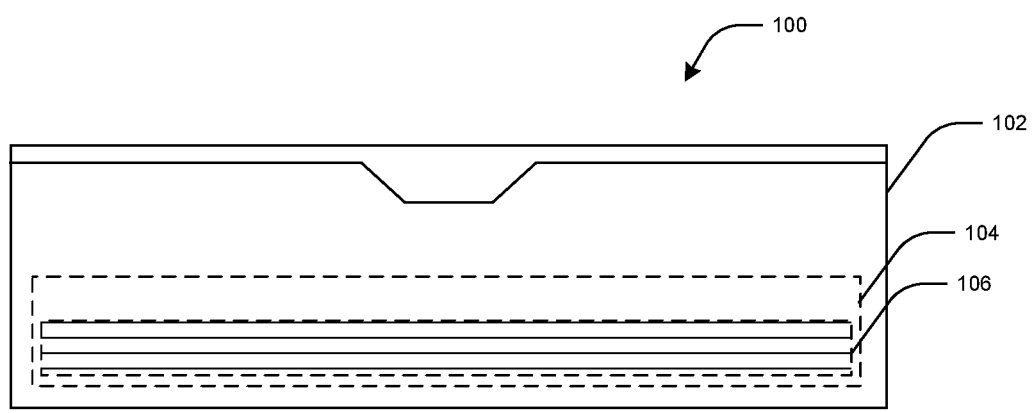
FIG. 1 is a schematic drawing of a biodegradable personal care system in accordance with one aspect of the present disclosure.

Individuals often purchase 3.4 ounces or smaller plastic bottles or small containers to carry their personal care and hygiene items. These plastic bottles and containers while convenient to carry should be disposed of in a trash receptacle or recycling receptacle following their use. These bottles and containers can often be thrown away and can end up in landfills where they can accumulate, can be thrown aside as litter, or the like, and can often take hundreds of years to degrade. The increased and continued use of plastic bottles and small containers can thus negatively affect the environment.

In some professions, workers such as police officers, firefighters, soldiers, emergency medical technicians, paramedics, and forest service personnel, have a need for personal care and hygiene items that are compact and can be readily disposed of. This is particularly true for fireman fighting wildfires, and soldiers working in remote locations, in some cases for extended periods of time. Accordingly, there is a need for personal care products contained in an environmentally friendly packaging.

Although the following detailed description contains many specifics for the purpose of illustration, a person of ordinary skill in the art will appreciate that many variations and alterations to the following details can be made and are considered included herein. Accordingly, the following embodiments are set forth without any loss of generality to, and without imposing limitations upon, any claims set forth. It is also to be understood that the terminology used herein is for describing particular embodiments only, and is not intended to be limiting. Unless defined otherwise, all technical and scientific terms used herein have the same meaning as commonly understood by one of ordinary skill in the art to which this disclosure belongs.

Furthermore, the described features, structures, or characteristics can be combined in any suitable manner in one or more embodiments. In the following description, numerous specific details are provided, to provide a thorough understanding of various embodiments. One skilled in the relevant art will recognize, however, that such detailed embodiments do not limit the overall concepts articulated herein, but are merely representative thereof. One skilled in the relevant art will also recognize that the technology can be practiced without one or more of the specific details, or with other components, layouts, etc. In other instances, well-known structures, materials, or operations may not be shown or described in detail to avoid obscuring aspects of the disclosure.

In this application, "comprises," "comprising," "containing" and "having" and the like can have the meaning ascribed to them in U.S. Patent law and can mean "includes," "including," and the like, and are generally interpreted to be open-ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open-ended term in this written description, like "comprising" or "including," it is understood that direct support should be afforded also to "consisting essentially of" language as well as "consisting of" language as if stated explicitly and vice versa.

As used herein, the term "substantially" refers to the complete or nearly complete extent or degree of an action, characteristic, property, state, structure, item, or result. For example, an object that is "substantially" impedes air exchange would mean that the object either completely impedes or nearly completely impedes air exchange. The exact allowable degree of deviation from absolute completeness may in some cases depend on the specific context. However, generally speaking, the nearness of completion will be so as to have the same overall result as if absolute and total impediment were obtained. The use of "substantially" is equally applicable when used in a negative connotation to refer to the complete or near complete lack of an action, characteristic, property, state, structure, item, or result. For example, a composition that is "substantially free of" toxins would either completely lack toxins, or so nearly completely lack toxins that the effect would be the same as if it completely lacked toxins. In other words, a system that is "substantially free of" an ingredient or element may still actually contain such item as long as there is no measurable effect thereof.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 1.5, 2, 2.3, 3, 3.8, 4, 4.6, 5, and 5.1 individually.

This same principle applies to ranges reciting only one numerical value as a minimum or a maximum. Furthermore, such an interpretation should apply regardless of the breadth of the range or the characteristics being described.

Reference throughout this specification to "an example," "an embodiment," or "an aspect" means that a particular feature, structure, or characteristic described in connection with the example, the embodiment, or the aspect is included in at least one example, one embodiment, or one aspect. Thus, appearances of phrases including "an example" or "an embodiment" in various places throughout this specification are not necessarily all referring to the same example, the same embodiment, or the same aspect. The terms example, embodiment, and aspect can all be used interchangeably herein.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein.

As used herein, an airtight container refers to a container that is materially and structurally configured to maintain the moisture level of the internal contents, thus precluding premature drying of the contents.

A "consumable personal care item" or "consumable hygiene item" refers to a personal care or hygiene item that upon use does not leave behind any material other than packaging that would require separate disposal, such as, lotion, antibacterial hand gel, liquid soap, and the like. A wipe is not considered to be a consumable personal care or hygiene item.

As used herein, a "natural environment" refers to an outdoor environment that is not controlled.

"Biodegradable" refers to a property of an object to be decomposed by sunlight, water, air, soil, and/living organisms in a natural environment. The object does not require human intervention to break down.

An initial overview of embodiments is provided below and specific embodiments are then described in further detail. This initial summary is intended to aid readers in understanding the disclosure more quickly, but is not intended to identify key or essential technological features, nor is it intended to limit the scope of the claimed subject matter.

The system presented herein includes biodegradable disposable packaging for consumable personal care items, such as a lotion and disposable personal care items that are not depleted following use, such as a wipe. The disposable packing and disposable personal care items can overcome the environmental issues surrounding the use of travel sized personal care and hygiene items.

In one example, the present disclosure provides a biodegradable personal care system including a biodegradable housing, a biodegradable airtight container positioned in the biodegradable housing, and a biodegradable moist wipe positioned inside the biodegradable airtight container. An exemplary system is illustrated in FIG. 1. A biodegradable personal care system 100 can include a biodegradable housing 102, a biodegradable airtight container 104, positioned in the housing 102, and a biodegradable moist wipe 106 positioned inside the airtight container 104.

In one example, the biodegradable housing ("housing") can have an interior space and can be configured to contain various personal care items. The amount of interior space can vary depending on the type and number of items contained in the housing. In one example, the interior space of the housing can be sufficiently large to hold an airtight container. In yet another example, the interior space of the housing can be sufficiently large to hold an airtight container, a dry wipe, a dry wipe container, a personal care item, or the like, including combinations thereof. In one example, the interior space of the housing can be sufficiently large to hold an airtight container, a dry wipe, a dry wipe container, or a combination thereof. In a further example, the interior space of the housing can be sufficiently large to hold an airtight container, a dry wipe, or a combination thereof.

The housing configuration can vary depending on a variety of factors, such as the housing design, the intended contents of the housing, and the like. In some aspects, the housing can be flexible, thus allowing it to conform to a subject's body, to the inside of a bag, a pocket, or the like. In yet other aspects, the housing can be rigid or can be flexible with at least one support that renders the housing rigid (i.e., a rigid portion). Such a rigid portion can provide protection by resisting punctures to the housing, thus protecting the housing as well as the components within the housing. The shape of the housing can also vary. For example, the housing can be a bag, a box, a pouch, a tote, a canister, an envelope, and the like. In one example, the housing can be a box.

In a further example, the housing can have an opening that can allow access to the interior space and, in some examples, the housing can further include a cover to close the opening. In other examples, the opening can be sealable or re-sealable. A sealable or re-sealable opening can include, for example, a zip-top, a tacky adhesive portion, a hook and loop fastener, an interlocking cover and opening, and the like. In yet another example, the housing can further include a carrying handle.

The housing can be comprised of any biodegradable material or composition and, in one example, can include abaca, hide, jute, cotton, a cotton blend, fique, paper, paperboard, liquid packaging board, biodegradable polymeric materials, or a combination thereof. In one example, the housing can be comprised of a cotton blend. In a further example, the material or composition of the housing can have certain properties or can be treated with a coating to impart certain properties, such as waterproofing, water-repelling, fire retarding, or the like.

In some examples, the biodegradable airtight container ("airtight container") can be positioned in the housing at any location that allows access to the contents of the airtight container, either while in the housing or following removal therefrom. The airtight container can be any type of container that is materially and structurally configured to maintain the moisture level of the internal contents, thus precluding premature drying of the internal contents.

The airtight container can be flexible, rigid, or a combination of flexible and rigid. In one example, the airtight container can be a box, a pouch, a sealed/sealable envelope, or the like. In some examples, the airtight container can be sized to fit in a pocket; while in other examples, the airtight container can be larger. In yet another example, the airtight container can have divided sections to separate and hold multiple moist wipes apart from one another. The multiple moist wipes can be the same type or different types of moist wipes. In some instances the airtight container can be coupled to the housing or in other instances, the airtight container can be a loose container that can be removed from the housing. In some examples, the material that the airtight container can be comprised of can be suitable for sealing in or blocking out moisture. In other examples a coating, lining, or other enclosure can be included that can allow for the interior of the airtight container to substantially seal in moisture and impede air exchange.

In some examples, the airtight container can be a single-use container; while in other examples, the airtight container can be a multiple use container. In some examples, a single-use airtight container can include a single moist wipe. In yet other examples, a single-use airtight container can include a seal that upon opening cannot be resealed. For example, a single use airtight container can be a pouch, pocket, or envelope with a sealed edge that can be designed to be ripped open.

In another example, the airtight container can be re-sealable to allow a user to carry and access multiple moist wipes over a period of time. In some examples, a seal can be used to close the airtight container. In other examples, the seal can be used to seal only the airtight portion of the container that seals in moisture and impedes air exchange. In one example, the seal can be interlocking plastic strips, a pressure sensitive adhesive, a clip, a clamp, a drawstring closure, a self-mating micro hooks, a hook to hook fastener, a hook and eye fastener, a tie, a re-closable package tape, or a combination thereof. In one example, the seal can include interlocking plastic strips and the interlocking plastic strips can be a zip-top, a slider seal, a zipper, a double zipper, a press-seal, re-sealable label, or a combination thereof.

The location of the seal can also vary. In some examples, the seal can be located at or along one or more edges of the airtight container. For example, the seal could be located at or near the top of the airtight container. In yet another example, the seal can be centrally located on a front surface or a back surface of the airtight container. In a further example, the seal could be located at, near, or along the side of the airtight container. In yet other examples, the seal could be located diagonally across or partially across a front surface or a back surface of the airtight container.

As has been described, the airtight container can be designed to include one or more moist wipes in an environment that provides protection against premature drying of the moist wipes. Various types of moist wipes can be included therein, which can depend on the preferences of the user, the intended use of the biodegradable personal care system, and the like. While any type of moist wipe is considered to be within the present scope, non-limiting examples can include a personal cleansing wipe, a deodorant wipe, a lotion wipe, a cooling wipe, a flushable wet wipe, a medication-containing wipe, an antiseptic wipe, an antimicrobial wipe, a burn ointment wipe, a glass cleansing wipe, a sunscreen wipe, an insect repellant wipe, and the like, including a combination thereof. In one example, the airtight container can include a moist wipe that is a personal cleansing wipe. In another example, the airtight container can include a moist wipe that is a deodorant wipe. In yet another example, the airtight container can include a moist wipe that is a cooling wipe. In a further example, the airtight container can include a moist wipe that is an antimicrobial wipe.

In some cases, the housing can include multiple different types of moist wipes contained together therein, either in different airtight containers or within the same airtight container. In one example multiple different types of moist wipes can be separated from one another in the same container by divisions in the biodegradable airtight container. While a given housing and/or airtight container can include any combination of types of moist wipes, including those listed above, in some cases specific types of moist wipes can be combined together for convenience. For example, one system can include a personal cleansing wipe, a deodorant wipe, a lotion wipe, and a combination thereof. This system can be used to refresh an individual, for example, during travel, while outdoors, after athletic activities, and/or in remote locations. In another example, a system can include an antiseptic wipe and a medication-containing wipe, such as, for example, a pain-relief medication, a burn cream, or an antibiotic. Such a system can be particularly useful for cleansing and relieving the pain associated with injuries, such as scraps and cuts. In yet another example, a system can include, a sunscreen wipe, an insect repellant wipe, a cooling wipe, and a combination thereof. This system can be useful during outdoor recreation or by workers in remote locations.

Figure 2:
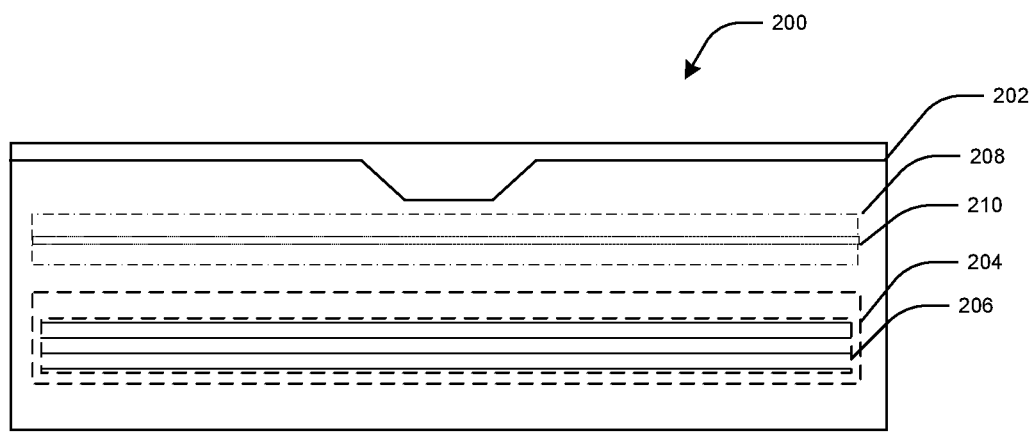
FIG. 2 is a schematic drawing of a biodegradable personal care system in accordance with one aspect of the present disclosure.
Figure 3:
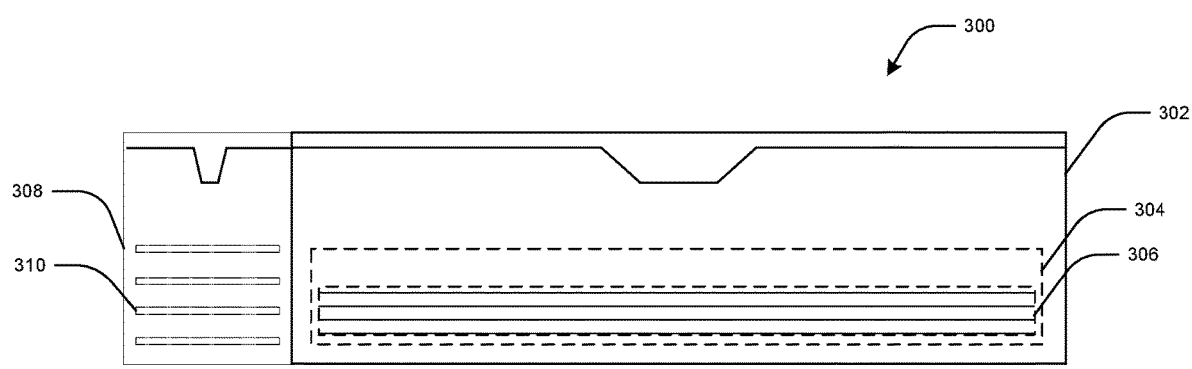
FIG. 3 is a schematic drawing of a biodegradable personal care system in accordance with one aspect of the present disclosure.
Figure 4A:
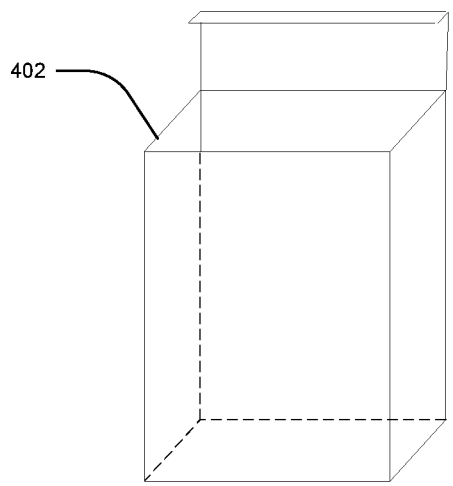
FIG. 4A is a schematic drawing of a biodegradable housing in accordance with one aspect of the present disclosure.
Figure 4B:
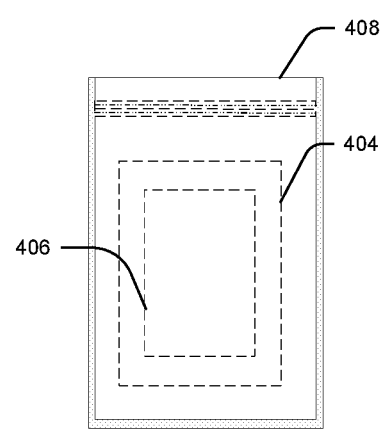
FIG. 4B is a schematic drawing of a dry container, airtight container, and moist wipe in accordance with one aspect of the present disclosure.

In some cases, a personal care system can further include a dry wipe, located within the housing, or located within a dry container. The dry container can be placed within the housing, within the airtight container, or coupled to the housing. For example, in the system shown in FIG. 2, the system 200 can include a housing 202, airtight container 204 positioned in the housing 202, moist wipe 206 positioned in the airtight container 204, dry container 208 positioned in the housing 202, and dry wipe 210 positioned in the dry container 208. In another example, as illustrated in FIG. 3, the system 300 can include dry wipe 310 located in a dry wipe container 308 that can be directly coupled to the housing 302. The housing can include the airtight container 304 and the moist wipe 306 positioned in the airtight container. In yet another example, the dry container can be coupled to the interior or the exterior of the housing. In some cases, the airtight container 404 including the moist wipe 406 can be positioned inside of the dry container 408 and placed within the housing 402. See FIGS. 4A and 4B.

The type of dry wipe can vary depending on the intended use of the system, the preferences of the user, and the like. In one example, the system can include toilet paper, a tissue, a napkin, a paper towel, a cleansing cloth, a gauze pad, an eye pad or patch, a cotton ball, a cotton swab, the like, and a combination thereof. In one specific example, the dry wipe can be toilet paper, such as a roll of toilet paper, a toilet paper sheet, a toilet paper square, or the like. In another example, the dry wipe can be a tissue. In yet another example, the dry wipe can be a cleansing cloth. The dry wipe can be any shape and size and can be shaped and sized for the shape of the container that the dry wipe is positioned in. In one example, the dry wipe can be biodegradable.

As previously mentioned, the dry wipe can be positioned in a dry wipe container. The dry wipe container is not particularly limited and can be flexible, rigid, or a combination thereof. The dry wipe container can be located inside the housing, either coupled to or as a loose container, or the dry wipe container can be located adjacent but exterior to the housing. In one example, the dry wipe container can be a bag, a box, a pouch, an envelope, or the like. In some examples, the dry wipe container can be biodegradable. In other examples, the dry wipe container can be sealable and/or re-sealable. When the dry wipe container is sealable and/or re-sealable the sealable and/or re-sealable portion can be a seal as previously described with respect to the airtight container and/or the housing.

The system can additionally include various other components that would be appropriate for a given type of personal care system. In some examples, the additional components can supplement the type of the system. For example, a system that is intended for medical care can further include a bandage, a butterfly closure, a blister cushion, an adhesive tape, a topical antibiotic cream pack, a pain relief pack, an antacid pack, an inhalant, a poison ivy cream pack, a wound seal powder pack, kinesiology tape, a tongue depressor, an aloe pack, an instant cold pack, an emergency blanket, a disposable glove, and the like, or a combination thereof. The additional components can be positioned anywhere in the system. In one example, the additional components can be positioned in the housing. In another example, the additional components can be positioned in the airtight container. In yet another example, the additional component can be positioned in the dry wipe container, when present.

As has been described, biodegradability can be important in some components of the personal care system. In some cases, all of the system components can be biodegradable, while in other cases, only a subset of the system components can be biodegradable. For example, the system could include a bandage that is not biodegradable. With respect to biodegradability, the biodegradable portion can include but is not limited to include, the housing, the airtight container, the moist wipe, the dry wipe, the dry wipe container, or any combination thereof. Biodegradable, as used herein, refers to a material or item that decomposes in a natural environment when exposed to sunlight, water, microbial activity, or a combination thereof. In one example, a system or a portion of the system can be from about 20% to about 60% degraded after 28 days when exposed in a natural environment to sunlight, water, microbial activity, or a combination thereof. In another example, a system or a portion of the system can be at least 60% degraded in 28 days when exposed in a natural environment to sunlight, water, microbial activity, or a combination thereof. In yet another example, a system or the portion of the system can be 100% degraded in six months when exposed in a natural environment to sunlight, water, microbial activity, or a combination thereof. In a further example, a system or a portion of the system can be 100% degraded in one year when exposed in its natural state to sunlight, water, microbial activity, or a combination thereof. With respect to percent degradation, degrade refers to federal government standards.

In other examples, the system can be compostable. With respect to compostability, the compostable portion can include the housing, the airtight container, the moist wipe, the dry wipe, the dry wipe container, or any combination thereof. As used herein, "compostable" or "compostability" means that the material or item breaks down into a soil conditioning material. In one example, the system or portions thereof can meet or exceed the standards for compostability as determined according to the American Society for Testing Materials (ASTM) standard D6400 dated May 15, 2012, ASTM standard D6868 dated Feb. 1, 2011, or a combination thereof.

In yet another example, a system or a portion thereof can be non-toxic to humans, animals, the natural environment, and the like, or a combination thereof. In some example, the system or portions thereof can be non-toxic when ingested. In one example, with respect to non-toxicity, the non-toxic portion can include but is not limited to include, the housing, the airtight container, the moist wipe, the dry wipe, the dry wipe container, or any combination thereof.

The described features, steps, or characteristics may be combined in any suitable manner in one or more embodiments. It will be apparent to those of ordinary skill in the art that numerous modifications in form, usage, and details of implementation can be made without the exercise of inventive faculty, and without departing from the principles and concepts of the invention presented herein.

What is claimed is:

1. A biodegradable personal care system, comprising:
   a biodegradable housing;
   a biodegradable dry wipe container positioned in the biodegradable housing;
   a biodegradable dry wipe positioned inside the biodegradable dry wipe container;
   a biodegradable airtight container positioned in the biodegradable dry wipe container; and
   a biodegradable moist wipe positioned inside the biodegradable airtight container.

2. The biodegradable personal care system of claim 1, wherein the biodegradable dry wipe container is re-sealable.

3. The biodegradable personal care system of claim 1, wherein the biodegradable dry wipe comprises toilet paper.

4. The biodegradable personal care system of claim 1, wherein the biodegradable dry wipe comprises a member selected from the group consisting of a toilet paper, a tissue, a napkin, a paper towel, a cleansing cloth, a gauze pad, an eye pad, an eye patch, a cotton ball, a cotton swab, and combinations thereof.

5. The biodegradable personal care system of claim 1, wherein the biodegradable moist wipe comprises a member selected from the group consisting of a personal cleansing wipe, a deodorant wipe, a lotion wipe, a cooling wipe, a flushable wet wipe, a medication-containing wipe, an antiseptic wipe, an antimicrobial wipe, a burn ointment wipe, a glass cleansing wipe, a sunscreen wipe, an insect repellant wipe, and combinations thereof.

6. The biodegradable personal care system of claim 1, wherein the biodegradable airtight container is re-sealable.

7. The biodegradable personal care system of claim 1, wherein the biodegradable housing is re-sealable.

8. The biodegradable personal care system of claim 1, wherein a member selected from the group consisting of, the biodegradable housing, the biodegradable dry wipe container, the biodegradable dry wipe, the biodegradable airtight container, the biodegradable moist wipe, and a combination thereof biodegrade from 20% to 60% in 28 days when exposed in a natural environment to sunlight, water, microbial activity, or a combination thereof.

9. The biodegradable personal care system of claim 1, wherein a member selected from the group consisting of the biodegradable housing, the biodegradable dry wipe container, the biodegradable dry wipe, the biodegradable airtight container, the biodegradable moist wipe, and a combination thereof is at least 60% degraded in 28 days when exposed in a natural environment to sunlight, water, microbial activity, or a combination thereof.

10. The biodegradable personal care system of claim 1, wherein a member selected from the group consisting of the biodegradable housing, the biodegradable dry wipe container, the biodegradable dry wipe, the biodegradable airtight container, the biodegradable moist wipe, and a combination thereof is 100% degraded in one year when exposed in a natural environment to sunlight, water, microbial activity, or a combination thereof.

11. The biodegradable personal care system of claim 1, wherein the biodegradable personal care system is non-toxic to a human, a natural environment, or a combination thereof.

12. The biodegradable personal care system of claim 1, wherein the biodegradable personal care system is compostable.

13. The biodegradable personal care system of claim 1, wherein the biodegradable personal care system meets the standards for biodegradability and compostability as determined according to ASTM D6400 dated May 15, 2012, ASTM D6868 dated Feb. 1, 2011, or a combination thereof.

* * * * *